(12) United States Patent
Wu et al.

(10) Patent No.: US 8,666,477 B2
(45) Date of Patent: Mar. 4, 2014

(54) METHOD AND SYSTEM FOR TRACKING OF A VIRTUAL ELECTRODE ON A CORONARY SINUS CATHETER IN FLUOROSCOPIC IMAGES

(75) Inventors: Wen Wu, East Windsor, NJ (US); Terrence Chen, Princeton, NJ (US); Norbert Strobel, Heroldsbach (DE); Gareth Funka-Lea, Cranbury, NJ (US); Dorin Comaniciu, Princeton Junction, NJ (US)

(73) Assignee: Siemens Aktiengesellschaft, München (DE)

( * ) Notice: Subject to any disclaimer, the term of this patent is extended or adjusted under 35 U.S.C. 154(b) by 42 days.

(21) Appl. No.: 13/413,721

(22) Filed: Mar. 7, 2012

(65) Prior Publication Data
US 2012/0232384 A1 Sep. 13, 2012

Related U.S. Application Data

(60) Provisional application No. 61/449,862, filed on Mar. 7, 2011.

(51) Int. Cl.
*A61B 5/05* (2006.01)
(52) U.S. Cl.
USPC .......................................... 600/424; 382/128
(58) Field of Classification Search
USPC ........................................................ 600/424
See application file for complete search history.

(56) References Cited

U.S. PATENT DOCUMENTS

| 5,845,004 A * | 12/1998 | Banjanin et al. ............... 382/128 |
| 6,104,944 A * | 8/2000 | Martinelli ...................... 600/424 |
| 6,590,999 B1 * | 7/2003 | Comaniciu et al. ........... 382/103 |
| 6,782,306 B2 * | 8/2004 | Yutkowitz ...................... 700/189 |
| 7,792,342 B2 | 9/2010 | Barbu et al. |

(Continued)

OTHER PUBLICATIONS

Mazouer et al. User-Constrained Guidewire Localization in Fluoroscopy, c. of SPIE, vol. 7259, pp. 72591 K-1-72591 K-9 (2009).*

(Continued)

*Primary Examiner* — Jonathan G Cwern
*Assistant Examiner* — Amelie R Gillman
(74) *Attorney, Agent, or Firm* — Michele L. Conover

(57) ABSTRACT

A method and system for detecting a virtual electrode (VE) on a coronary sinus (CS) catheter in a fluoroscopic image sequence is disclosed. User inputs indicating locations of CS catheter electrodes and a location of a VE are received. A catheter electrode model and a VE part model is initialized in a first frame of the fluoroscopic image sequence. The VE is tracked by detecting electrode position candidates and catheter body point candidates in the subsequent frames of the fluoroscopic image sequence using respective trained detectors, tracking the catheter electrode model in the subsequent frames based on the detected electrode position candidates, generating VE part hypotheses in the subsequent frames based on detection of the most proximal electrode (MPE) in each subsequent frame, calculating a probability score for each of the VE part hypotheses, and selecting an VE part hypothesis with the highest probability score.

28 Claims, 7 Drawing Sheets

(56) References Cited

U.S. PATENT DOCUMENTS

| | | | |
|---|---|---|---|
| 2003/0235337 A1* | 12/2003 | Paragios et al. | 382/215 |
| 2005/0152617 A1* | 7/2005 | Roche et al. | 382/294 |
| 2007/0189580 A1* | 8/2007 | Slabaugh et al. | 382/103 |
| 2007/0270692 A1* | 11/2007 | Barbu et al. | 600/431 |
| 2008/0080754 A1 | 4/2008 | Barbu et al. | |
| 2008/0317317 A1* | 12/2008 | Shekhar et al. | 382/131 |
| 2009/0062641 A1* | 3/2009 | Barbu et al. | 600/424 |
| 2009/0163800 A1* | 6/2009 | Xu et al. | 600/424 |
| 2009/0279767 A1 | 11/2009 | Kukuk et al. | |
| 2010/0121181 A1 | 5/2010 | Wang et al. | |
| 2012/0069003 A1 | 3/2012 | Birkbeck et al. | |
| 2012/0070046 A1 | 3/2012 | Wu et al. | |

OTHER PUBLICATIONS

Klemm Hu, et al. Catheter motion during atrial ablation due to the beating heart and respiration: Impact on accuracy and spatial referencing in three-dimensional mapping. Heart Rhythm (2007).*

* cited by examiner

METHOD AND SYSTEM FOR TRACKING OF A VIRTUAL ELECTRODE ON A CORONARY SINUS CATHETER IN FLUOROSCOPIC IMAGES

This application claims the benefit of U.S. Provisional Application No. 61/449,862, filed Mar. 7, 2011, the disclosure of which is herein incorporated by reference.

BACKGROUND OF THE INVENTION

The present invention relates to detection and tracking of a coronary sinus catheter in fluoroscopic images, and more particularly, to detecting and tracking a virtual electrode on a coronary sinus catheter in fluoroscopic images to assist in atrial fibrillation ablation treatment.

Atrial fibrillation (AF) is a rapid, highly irregular heartbeat caused by abnormalities in the electrical signals generated by the atria of the heart. It is the most common cardiac arrhythmia (abnormal heart rhythm) and involves the two upper chambers (atria) of the heart. Surgical and catheter-based therapies have become common AF treatments throughout the world. Catheter ablation modifies the electrical pathways of the heart in order to treat AF. To measure electrical signals in the heart and assist the operation, different catheters are inserted into a patient's blood vessels and guided to the heart. The entire operation is guided with real-time fluoroscopic images. The integration of static tomographic volume renderings into three-dimensional catheter tracking systems has introduced an increased need for mapping accuracy during AF procedures. However, the heart is not a static structure, and the relative motion of mapping and reference catheters can lead to significant displacements. Current technologies typically concentrate on gating catheter position to a fixed point in time within the cardiac cycle based on an electrocardiogram (ECG), without compensating for respiration effects. The often advocated static positional reference provides an intermediate accuracy in association with ECG gating.

Tracking electrodes of a coronary sinus (CS) catheter (the catheter inside the CS) has been shown to be effective to compensate respiratory and cardiac motion for 3D overlay to assist physicians when positioning the ablation catheter. However, conventional tracking algorithms encounter difficulties in the presence of large image variations, nearby similar structures, and cluttered background.

BRIEF SUMMARY OF THE INVENTION

Embodiments of the present invention provide a robust and fast method to track a virtual electrode on a coronary sinus (CS) catheter that is more proximal than the most proximal electrode in a sequence of fluoroscopic images. Embodiments of the present invention first track the CS catheter electrodes using a learning-based algorithm, and then fuse available tracking information in order to track the virtual electrode in the sequence of fluoroscopic images.

In one embodiment of the present invention, user inputs indicating locations of CS catheter electrodes and a location of a virtual electrode (VE) are received. A VE part of the catheter body, between the most proximal electrode and the VE, is detected. A catheter electrode template and a VE part template are initialized in a first frame of a fluoroscopic image sequence based on input locations of a plurality of CS sinus catheter electrodes and an input location of a VE in the first frame. The VE is tracked in a second frame of the fluoroscopic image sequence by detecting electrode position candidates and catheter body point candidates in the second frame using respective trained detectors, tracking the catheter electrode template in the second frame based on the detected electrode position candidates, generating VE part hypotheses in the second frame based on a most proximal electrode (MPE) in the second frame, calculating a probability score for each of the VE part hypotheses, and selecting one of the VE part hypotheses as the VE part template in the second frame based on the probability score.

These and other advantages of the invention will be apparent to those of ordinary skill in the art by reference to the following detailed description and the accompanying drawings.

DETAILED DESCRIPTION

The present invention relates to a method and system for tracking a virtual electrode on a coronary sinus (CS) catheter in fluoroscopic images. Embodiments of the present invention are described herein to give a visual understanding of the CS catheter virtual electrode tracking method. A digital image is often composed of digital representations of one or more objects (or shapes). The digital representation of an object is often described herein in terms of identifying and manipulating the object. Such manipulations are virtual manipulations accomplished in the memory or other circuitry/hardware of a computer system. Accordingly, is to be understood that embodiments of the present invention may be performed within a computer system using data stored within the computer system.

Tracking the coronary sinus (CS) catheter can help compensate respiratory and cardiac motion for 3D overlay to assist in positioning an ablation catheter in atrial fibrillation (AF) treatments. However, during AF interventions, the CS catheter performs rapid motion and non-rigid deformation due to the beating heart and respiration. Therefore, motion of the CS catheter may not be accurate enough for motion compensation. Embodiments of the present invention track a virtual electrode (VE) on the CS catheter that is a non-existing electrode on the CS catheter more proximal than any real electrode. The successful tracking of a VE can provide more accurate respiratory motion information than tracking the real electrodes. To achieve the VE tracking in a fluoroscopic image sequence, the CS catheter is first modeled as a set of electrodes which are tracked using a learning-based approach. Then, the tracked catheter electrodes are used to generate hypotheses for tracking a VE. Model-based hypotheses are fused and validated by a robust Bayesian-based hypothesis matching framework.

Figure 1:
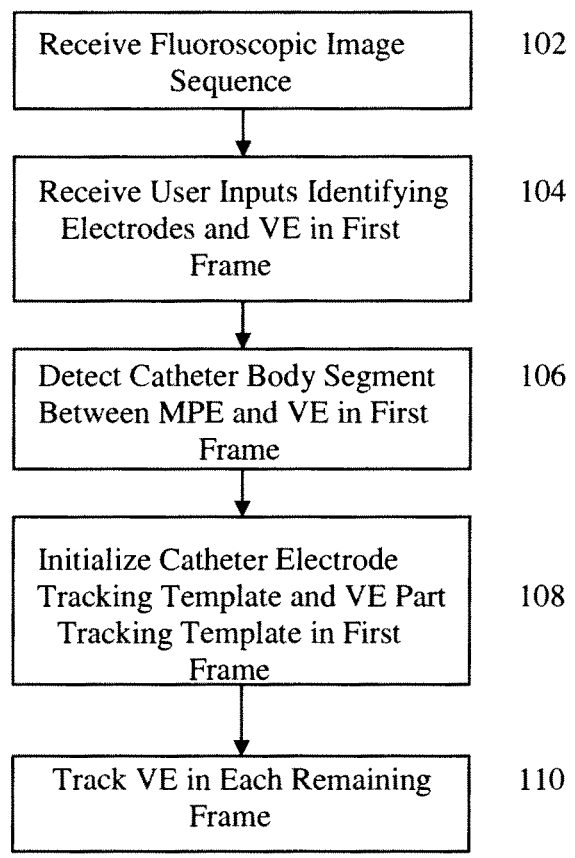
FIG. 1 illustrates a method for tracking a virtual electrode (VE) on a CS catheter in a fluoroscopic image sequence according to an embodiment of the present invention.

FIG. 1 illustrates a method for tracking a virtual electrode (VE) on a CS catheter in a fluoroscopic image sequence according to an embodiment of the present invention. In the description of the method of FIG. 1, notations are used as follows. Z denotes an image observation, D denotes image intensity data, C denotes a catheter electrode set, and V denotes a set of spline control points representing the VE part of the CS catheter (i.e., the catheter body between the most proximal electrode (MPE) and the VE). The subscript t denotes the t-th frame. Assuming there are K electrodes $\{e^i, i=1,\ldots,K\}$ on the catheter, $e^1$ and $e^K$ represent the tip and the MPE, respectively. There are L spline control points in V, $\{v^i, i=1,\ldots,L\}$, and $v^1$ and $v^L$ represent the locations of the MPE and the VE, respectively.

As illustrated in FIG. 1, at step 102, a fluoroscopic image sequence is received. The fluoroscopic image sequence is a sequence of fluoroscopic (x-ray) images acquired over a time period. The fluoroscopic image sequence can be received directly from an x-ray imaging device. It is also possible that the fluoroscopic image sequence can be received by loading a previously stored fluoroscopic image sequence.

At step 104, user inputs are received identifying locations of CS catheter electrodes and a VE in a first frame of the fluoroscopic image sequence. In particular, using a computer input device, such as a mouse, a user can click on the locations of the real CS catheter electrodes and the VE in the first frame of the fluoroscopic image sequence. In an advantageous implementation, a user can click on the real electrodes in order from the catheter tip to the most proximal electrode (MPE) and then lastly, select the VE. The user can select any point on the CS catheter that is more proximal to the proximal end of the catheter than the MPE.

Figure 2:
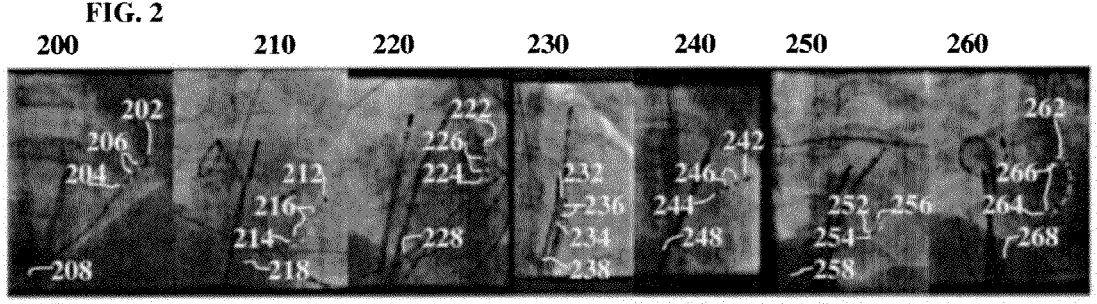
FIG. 2 illustrates CS catheter electrodes and virtual electrodes in exemplary fluoroscopic images.

FIG. 2 illustrates CS catheter electrodes and virtual electrodes in exemplary fluoroscopic images. As shown in FIG. 2, images 200, 210, 220, 230, 240, 250, and 260 show CS catheter tips 202, 212, 222, 232, 242, 252, and 262, MPEs 204, 214, 224, 234, 244, 254, and 264, other CS electrodes 206, 216, 226, 236, 246, 256, and 266, and VEs 208, 218, 228, 238, 248, 258, and 268, respectively.

At step 106, a catheter body segment between the MPE and the VE is detected in the first frame based on the user inputs. From the user initialization, the VE part of the CS catheter is detected. The "VE part" refers to a segment of the CS catheter between the MPE and the VE. In an advantageous implementation, $V_0$ (the VE part in the first frame) is detected using the method described in Mazouer et al., "User-Constrained Guidewire Localization in Fluoroscopy", *Proc. of SPIE, Vol.* 7259, pp. 72591K-1-72591K-9 (2009), which is incorporated herein by reference. This method is used to improve a localization result of a wire-like object interactively by adding user inputs. In order to minimize the manual effort required, each input point is designed to be a single click on the wire-like object. The first two points define the beginning and the end of the wire-like object. An additional point is provided if the wire segment is still missed in the localization result. More points can be provided until the user obtains a satisfactory result. The detection engine to execute this method includes three main components—a segment detector, a curve classifier, and dynamic programming. In the detection of the VE part in step 106, the detection algorithm is provided with two points, the MPE and VE, and the algorithm obtains the initial VE part $V_0$ based on the two user initialized points.

At step 108, tracking templates are initialized in the first frame for the CS catheter electrodes template and the VE part of the CS catheter. In particular, a CS catheter electrode tracking template and a VE part tracking template are initialized in the first frame. The CS catheter electrode tracking template and the VE part tracking template are used to track the CS catheter electrodes and the VE part, respectively, in each remaining frame of the fluoroscopic image sequence. In order to initialize the tracking templates for the CS catheter electrodes and the VE part, a tracking strategy is selected for each based on the catheter shape, the number of electrodes, and the size of the VE part. The tracking strategy refers to whether to model the template using a single model or multiple models.

The CS catheter electrode tracking template can be implemented using one or more CS catheter electrode models based on the number of electrodes identified in the first frame. According to an advantageous implementation, a single part electrode model is used if there are less than or equal to eight electrodes, a two part electrode model is used if there greater than eight and less than or equal to 16 electrodes, and a three part electrode model is used if there are greater than 16 electrodes. The decomposition of the identified electrodes into two or three parts may be based on a curvature analysis along the CS catheter shape, which is a spline formed by the identified electrodes. In one possible implementation, the highest curvature points on the spline formed by the electrodes can be selected as points to divide the spline into multiple parts. It is also possible to constrain the decomposition of the electrodes into multiple parts based on the locations of the electrodes in the first frame to ensure that the electrodes are divided relatively evenly between the parts. A catheter electrode model is stored for each part based on the input electrode locations. In particular, for each part, the coordinates of the CS catheter template and the corresponding intensity values for each point in the first frame are stored by densely sampling points in normal directions along a spline constructed by the user input electrode center points. An electrode mask is also constructed for each part based on the relative locations of the electrodes. The electrode mask facilitates summing up electrode detection scores at individual electrode locations during tracking. In cases in which electrode models are stored for multiple parts, the electrode models can be ordered, for example from the catheter tip to the most proximal electrode.

Regarding the VE part tracking template, the VE part can be divided into two segments if the length of the VE part is greater than a threshold value (e.g., 40 mm). The two segments can be divided at a maximum curvature point on the VE part, and the maximum curvature point can be included into each segment model. The model for the VE part (or each segment of the VE part) is constructed using a plurality control points sampled along the detected VE part in the first frame. The coordinates of the control points and the corresponding intensity values for the control points in the first frame are stored. The template for the VE part is obtained from the first frame and a system of coordinates that is relative to the shape representation of the VE part.

At step 110, the VE is tracked in each frame of the fluoroscopic image sequence using the CS catheter electrodes tracking template and the VE part tracking template. The VE is tracked in each frame by first tracking the CS catheter electrodes in each frame and then tracking the VE based on the Results of the CS catheter electrode tracking.

Figure 3:
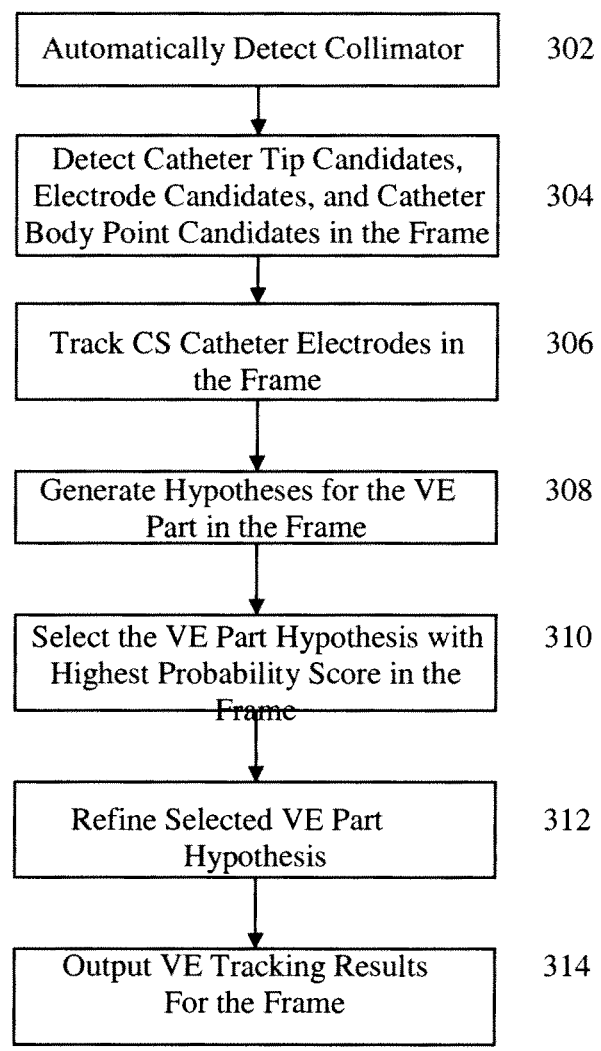
FIG. 3 illustrates a method for tracking a virtual electrode in a frame of a fluoroscopic image sequence according to an embodiment of the present invention.

FIG. 3 illustrates a method for tracking a VE in a frame of a fluoroscopic image sequence according to an embodiment of the present invention. The method of FIG. 3 can be repeated for each remaining frame of the fluoroscopic image sequence to implement step 110 of FIG. 1. As illustrated in FIG. 3, at step 302, a collimator is automatically detected. The collimator is a black border of a fluoroscopic image. The collimator can be automatically detected using a trained border detector. The trained border detector can be trained using a machine-learning algorithm based on annotated training data. The location of the collimator is detected and stored. This allows the method to recognize cases in which the VE is obscured by the collimator.

At step 304, catheter tip candidates, electrode candidates, and catheter body point candidates are detected in the current frame using respective trained detectors. In particular, trained detectors to detect catheter tip candidates, electrode candidates, and catheter body points are trained by learning respective discriminative models based on appearance and contextual features of the CS catheter tip, electrodes, and body points, respectively, using annotated training data.

Accurate detection of catheter electrode candidates and body point candidates not only provides robust estimation of the catheter position, but also helps prune the search space for tracking the catheter and the VE part. Further, such detection is useful in predicting when the catheter moves out of or back into the image. The CS catheter tip candidates, electrode candidates, and body point candidates are detected as points (x, y), parameterized by their position, which is detected using respective trained binary classifiers. In one implementation, the trained classifiers each use one hundred thousands of Haar features centered in a window of size $W_x \times W_y$ pixels (e.g., 69×69). Each classifier can be a probabilistic boosting tree (PBT) trained from annotated training data, and each classifier can output a probability P(d=(x,y)|D) for each point in the image. The catheter electrodes have a strong appearance in terms of content and context and can be detected more reliably than the catheter body points. For each classifier (catheter tip, electrode, and catheter body), points in the image having a probability above a threshold value are classified as positive. The set of detected electrodes and tips at in each frame is processed using a non-maximal suppression algorithm that combines clustered detections. At each frame, at most I electrode candidates and J tip candidates are kept as the detection results, which are used for tracking the catheter. Any detected candidates at a distance of at least $d_{min}$ from the initial CS catheter are removed, since the heart has only a limited range of motion due to breathing.

Figure 4:
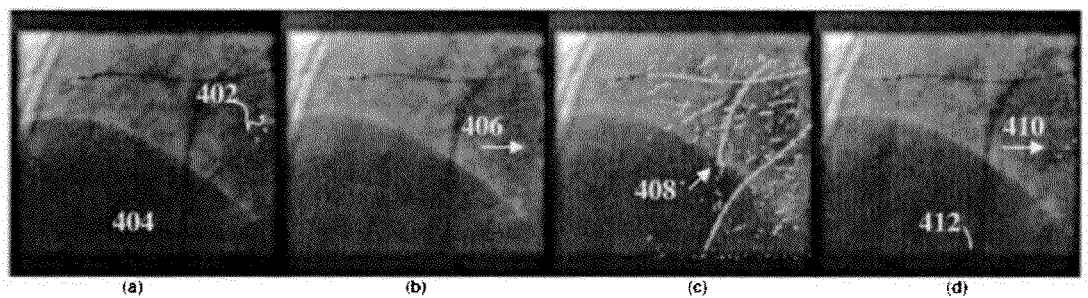
FIG. 4 illustrates exemplary user initialization of CS catheter electrodes and a virtual electrode, detection of electrode and catheter body candidate detection, and tracking results.

FIG. 4 illustrates exemplary results of CS catheter electrode and body candidate detection. As shown in FIG. 4, image (a) shows CS catheter electrodes 402 and VE 404 input by a user. Image (b) shows automatically detected electrode candidates 406 after non-maximal suppression. As shown in image (c), automatically detected catheter body points 408 are highlighted.

Figure 5:
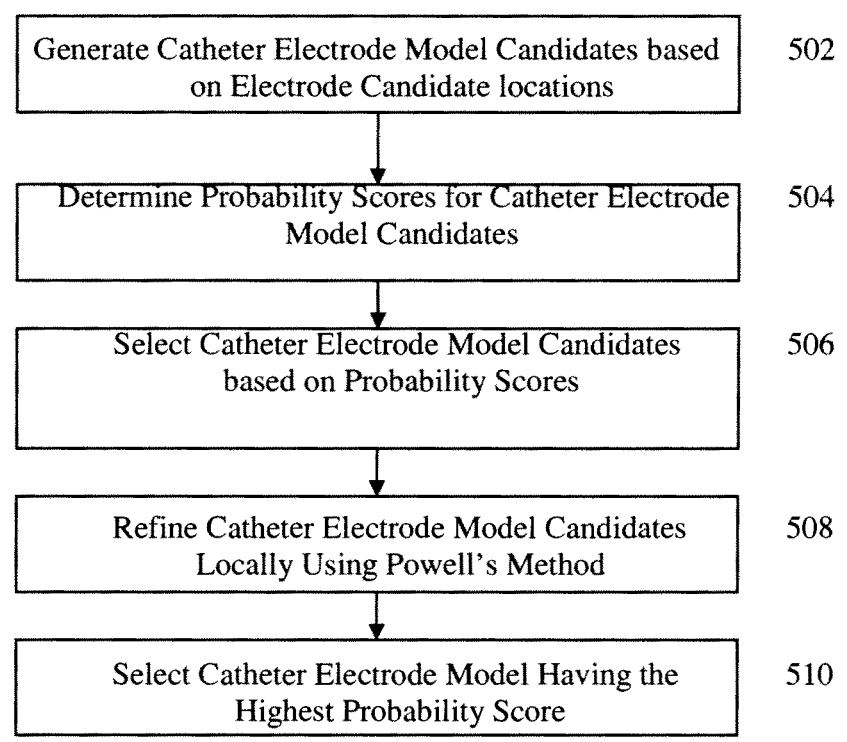
FIG. 5 illustrates a method of tracking a CS catheter model in a frame of a fluoroscopic image sequence according to an embodiment of the present invention.

Returning to FIG. 3, at step 306, the CS catheter electrodes are tracked in the frame based on the detected CS catheter tip and CS catheter electrode candidates. In an advantageous embodiment, the CS catheter electrodes are tracked using the methods described in U.S. patent application Ser. No. 13/229,855, entitled "Method and System for Detection and Tracking of Coronary Sinus Catheter Electrodes in Fluoroscopic Images", filed Sep. 12, 2011, the disclosure of which is incorporated herein by reference. FIG. 5 illustrates a method of tracking a CS catheter model in a frame of a fluoroscopic image sequence according to an embodiment of the present invention. The method of FIG. 5 can be used to implement step 306 of FIG. 3. As illustrated in FIG. 5, at step 502, electrode model candidates are generated based on the detected electrode (and catheter tip) candidates in the frame.

In particular, for each of K electrode candidate positions detected in step 304, E (the number of electrodes) electrode model hypotheses are generated by translating each electrode in the electrode tracking template (initialized in the first frame) to the respective electrode candidate position. This results in K*E electrode model hypotheses. A set of electrode model candidates is generated for each catheter electrode model hypothesis by applying an affine transformation of the catheter electrode model candidate by varying translation (Tx, Ty), scale (Sx, Sy), rotation (R), and skew (Sk). This results in a large number of catheter electrode model candidates (tracking hypotheses), each of which is a complete set of coordinates corresponding to locations of all of template points in the catheter electrode model.

At step 504, a probability score is determined for each of the electrode model candidate. The probability score is based on a comparison of the intensity values of the electrodes in the catheter electrode model hypothesis and the electrode model initialized in the first frame, as well as the detection scores for the electrodes in the model hypothesis using the trained electrode detector. In particular, the probability (confidence) score for each catheter electrode model candidate can be expressed as:

$$P(C|M_i) = P_{Img}(C|M_i) \cdot P_{Det}(C|M_i) \quad (1)$$

where C denotes the CS catheter and $M_i$ denotes the i-th candidate model. $P_{Img}(C|M_i)$ is the matching score given image intensity evidence and computed by normalized cross correlation between the intensity values of the template points in the candidate model and the intensity values of the template points in the electrode model initialized in the first frame. $P_{Det}(C|M_i)$ represents the probability value given by electrode detection scores for the electrodes in the candidate model. The stored electrode mask for the initialized electrode model can be placed on the current frame using the affine parameters [Tx, Ty, Sx, Sy, R, Sk] of the current candidate model. The trained electrode detector can then calculate the probability of being an electrode for each electrode location given by the electrode mask. The probabilities of each electrode can be summed to calculate $P_{Det}(C|M_i)$.

Alternatively, the probability (confidence) score for each catheter electrode model candidate can also be expressed as:

$$P(C|M_i) = (1-a) \cdot P_{Img}(C|M_i) + a \cdot P_{Det}(C|M_i) \quad (2)$$

where a is a weight whose value is between 0 and 1, and it can also be defined as $a = 1/(1+e^{-P_{Img}(C|M_i)})$. Both score calculations shown in above equations have been implemented by the present inventors and are effective.

At step 506, a number of catheter electrode model candidates are selected having the highest probability scores. For example, a predetermined number of electrode model candidates having the highest probability scores may be selected. Alternatively, all catheter electrode model candidates having a probability score over a certain threshold may be selected. It is also possible that a predetermined number of catheter electrode model candidates having the highest probability scores over a certain threshold are selected. In an advantageous implementation, non-maximal suppression can be used to reduce the number of catheter electrode model candidates prior to selecting the catheter electrode model candidates having the highest scores.

At step 508, the selected electrode model candidates are refined to find the local maximum probability score for each candidate. In order to refine matching locally, Powell's method can be applied to find the local maximum probability score. Powell's method utilizes a bidirectional search along a search vector for each affine parameter in turn to maximize a candidate model's probability score. This is repeated a certain number of times or until the method converges and no further improvement is possible. This can achieve minor adjustments in the affine parameters of a candidate model that result in an improved probability score.

At step 510, a catheter electrode model is detected in the frame by selecting the catheter electrode model candidate having the highest probability score. This catheter electrode model candidate gives the locations of all of the electrodes in the frame. The method of FIG. 5 illustrates tracking of a single catheter model in a frame. If the CS catheter tracking template initialized in the first frame is a multi-part model, the method each part can be sequentially first tracked from the catheter tip to the MPE, with the last detected electrode in the first part being used as rotation center to generate hypotheses for the second part, and so on, resulting in detection of a first combined electrode model. Each part is then sequentially tracked in the opposite direction, resulting in a second combined electrode model. The combined electrode model having the highest probability score is then selected as the electrode model for the frame.

Returning the FIG. 3, at step 308, hypotheses are generated for the VE part in the current frame based on the tracked location of the MPE using the VE part tracking template. The non-rigid nature of the CS catheter means that motion of the VE has to be represented in a high dimensional space. Instead of an exhaustive search which is also not reliable, embodiments of the present invention utilize a low dimensional representation that approximates the VE part with a small error. Then a number of shape hypotheses are generated for finding the VE in the current frame, with each shape hypothesis implicitly containing the template deformation. The hypotheses are then evaluated (in step 310) by template matching combined with detection probability in a Bayesian framework.

After the user initialization, the tracking template of the VE part is obtained, as described above. The template is obtained from the first frame and a system of coordinates that is relative to the shape representation.

Given the MPE location tracked in the current frame, hypotheses for tracking the VE part are generated as candidate shapes in the current frame. Given the detected catheter body point candidates in the current frame, the following scheme is used to generate hypotheses. According to an advantageous embodiment, the set of hypotheses is generated by parametrically manipulating the VE part based on the MPE location. The VE part model $V_{t-1}$ from the previous frame is used as an input for the hypotheses generation in the current frame. It is to be understood that the VE part model from the first frame is the initialized tracking template. The VE part model is represented as a set of control points. A seed hypothesis $\overline{V}_t$ is generated by translating the VE part model $V_{t-1}$ from the previous frame to the current frame. More specifically, the seed hypothesis $\overline{V}_t$ is generated by translating the MPE (i.e., first control point) of $V_{t-1}$ to the detected $MPE_t$. This translates $V_{t-1}$ such that the first control point $v^1$ is located at the location of the MPE in the current frame. From the seed hypothesis $\overline{V}_t$, $MPE_t$ (i.e., the first control point $v^1$ of $\overline{V}_t$) is used as a transformation center and a set of affine transformation are applied to generate tracking hypotheses as:

$$V_t = A \cdot \overline{V}_t, A = \begin{bmatrix} C & d \\ 0^T & 1 \end{bmatrix}. \tag{3}$$

This strategy is effective in generating effective tracking hypotheses, and varying the parameters of the affine transformation with the location of the MPE as a rotation center results in a pool of tracking hypotheses. Since each tracking hypothesis includes a set of control points, each hypothesis is a shape hypothesis for the VE part. As described above, a long VE part can be divided into two segments, and in this case hypotheses are generated for each segment and constrained to be coherent. In particular, if the length of $V_0$ is smaller than 40 mm, the VE part is modeled as a single segment; otherwise, the point with maximal curvature in $V_0$ can be identified and $V_0$ can be approximated as two segments joined at the maximum curvature point. In the case of two segments, let $\xi(v^i)$ represent the curvature of the catheter body at point i, and the algorithm finds $v^i = \arg\max_i \xi(v^i)$ as the joint point and cuts the VE part tracking template $V_0$ into two segments (sets), $\{v_0^1, v_0^2, \ldots, v_0^j\}$ and $\{v_0^j, v_0^{j+1}, \ldots, v_0^L\}$. At each frame tracking is performed on the first segment using the tracking method illustrated in FIG. 3. After the first segment has been tracked the location of $v^j$ serves as a transformation center to generate and evaluate the tracking hypotheses of the second segment as illustrated in 308, 310 and 312 in FIG. 3. Accordingly, the dimension of the search space for the second segment is much lower and the search is faster. Using the joint body point $v^j$ in both segments also guarantees one integrated VE part as an output.

At step 310, one of the VE part hypotheses is selected as the VE part template in the current frame. According to an advantageous implementation, the VE part hypotheses are evaluating using a Bayesian framework. In particular, a probability score is calculated for each hypothesis. The probability score is based on a comparison of the intensity values of the control points in the VE part hypothesis and the VE part tracking template initialized in the first frame, as well as the detection scores for the control points in the VE part hypothesis detected using the trained catheter body detector. The overall goal for evaluating the tracking hypotheses of the VE part is to select one of the VE part hypotheses to maximize the posterior probability:

$$\hat{V}_t = \underset{V_t}{\operatorname{argmax}} P(\overline{V}_t \mid Z_{0 \ldots t}) \tag{4}$$

where $Z_{0 \ldots t}$ is the image observations from the 0 to t-th frames. By assuming a Markovian representation of the VE part motion, equation (4) can be expanded as:

$$\hat{V}_t = \underset{V_t}{\operatorname{argmax}} P(Z_t \mid V_t) P(V_t \mid V_{t-1}) P(V_{t-1} \mid Z_{0 \ldots t-1}). \tag{5}$$

Equation (5) essentially combines two parts: the likelihood term, $P(Z_t|V_t)$, which is calculated as a combination of detection probability and template matching, and the prediction term $P(V_t|V_{t-1})$, which captures the motion smoothness.

Figure 6:
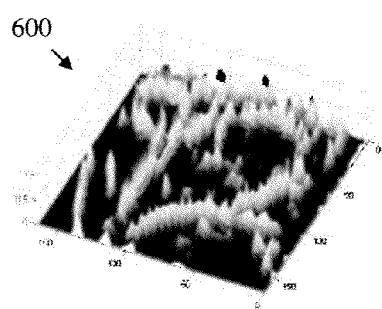
FIG. 6 illustrates an example of a catheter body probability map.

To maximize tracking robustness, the likelihood term $P(Z_t|V_t)$ is estimated by combining the VE part detection probability and the template matching as follows:

$$P(Z_t|V_t) = P(B_t^* | V_t) \cdot P(T_t | V_t) \tag{6}$$

where $B_t^*$ is the estimated probability measure about catheter body segments at the t-th frame that assists estimation of $V_t$, and the detection term $P(B_t^*|V_t)$ is defined in terms of a part model as:

$$P(B_t^* | V_t) = \sum_{i=1}^{L} P(B_t^* | v_t^i), \quad (7)$$

where $P(B_t^*|v_t^i)$ represents the probability at each body point determined using the catheter body detector. FIG. 6 illustrates an example of a catheter body probability map 600. The catheter body probability map 600 is generated by calculating the probability value for each pixel in a frame using the trained catheter body detector. $P(T_t|V_t)$ is the intensity normalized cross-correlation between the VE part template and the image band expanded by $V_t$.

The prediction term $P(V_t|V_{t-1})$ in equation (5) is modeled as a zero-mean Gaussian distribution and $$N(0, \sigma_T): P(V_t | V_{t-1}) = P\left(\frac{d(V_t - V_{t-1}^+)}{d(V_t - V_{t-1}^-)}\right),$$

and $d(V_t-V_{t-1}^+)$ and $d(V_t-V_{t-1}^-)$ measure the spine distance from $V_t$ to positive and negative models at the (t−1)-th frame with $\sigma_T$ learned from the training data.

In cases in which the VE part is divided into two local segments based on the part length and shape, as described above, the results of tracking two segments are evaluated by the overall matching score, which combines each segment's score as:

$$P(Z_t | V_t) = \sum_{\alpha=1}^{2} \epsilon_\alpha \cdot P(Z_t | S_\alpha) \quad (8)$$

where $P(Z_t|S_\alpha)$ is calculated by Equation (6), $\epsilon_\alpha$ is calculated as the ratio of the segment length to the sum of the two segment lengths, and $\alpha$ is the index of segments.

Returning to FIG. 3, at step 312, the VE part template selected in the frame is refined. The shape of the VE part can deform non-rigidly due to the impact of cardiac and respiratory motion, and projection angulation. In order to handle non-rigid deformation, a first strategy described above is to divide the VE part into two local segments based on the part length and shape and to evaluate the hypotheses of the two segments as described above in Equation (8). Furthermore, in step 312, the VE part is refined by non-rigid tracking since the VE may appear at locations where the catheter body segmented is distorted. In order to achieve an effective combination of speed and accuracy, the control points ($v^i$) are sequentially deformed along normal directions, starting from the MPE to obtain the final location of the VE and the shape of the VE part. The shape of the VE part is used as an adaptive model to track the VE part in the next frame.

Foreground and background structures in fluoroscopy are constantly changing and moving. In order to cope with the changing structures dynamically, the VE part model in the frame is updated online by:

$$T_t=(1-\phi_\omega) \cdot T_t + \phi_\omega \cdot D(V_t), \text{ if } P(Z_t|V_t) > \phi, \quad (9)$$

where $T_t$ represents the VE part template in frame t and $D(V_t)$ is the image patch obtained at frame t based on the output $V_t$. In one possible implementation, $\phi_w=0.1$ and $\phi_w=0.05$.

At step 314, the tracking results for the current frame is output. In particular, the location of the VE, the VE part model for the current frame, and the updated motion profile obtained by tracking the location of the VE over multiple frames may be output. Returning to FIG. 4, image (d) of FIG. 4 shows tracked electrodes 410 and VE 412 resulting from applying the tracking method of FIG. 3.

Figure 7:
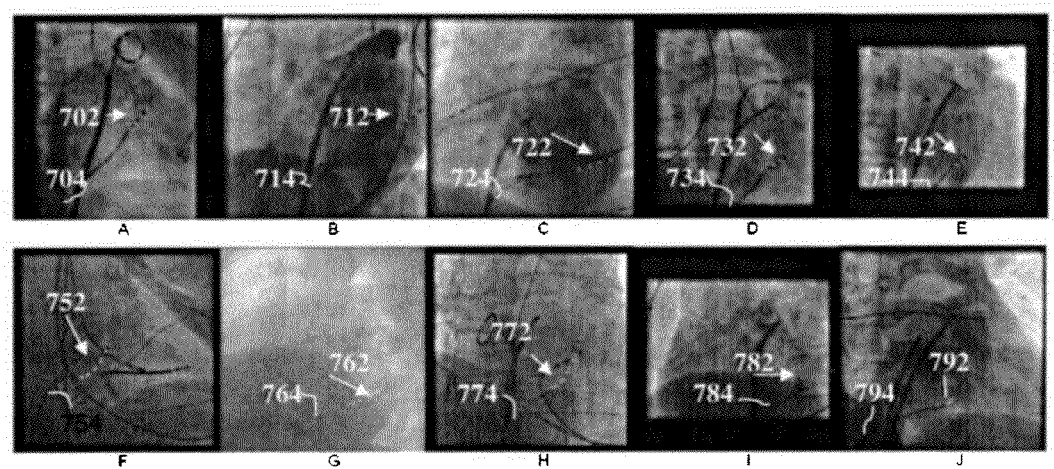
FIG. 7 illustrates examples of virtual electrode tracking results.

FIG. 7 illustrates examples of VE tracking results. As illustrated in FIG. 7, images A-J show tracked CS catheter electrodes 702, 712, 722, 732, 742, 752, 762, 772, 782, and 792 and tracked virtual electrodes 704, 714, 724, 734, 744, 754, 764, 774, 784, and 794 respectively, obtained using the methods described in above in FIGS. 1, 3, and 5.

Figure 8:
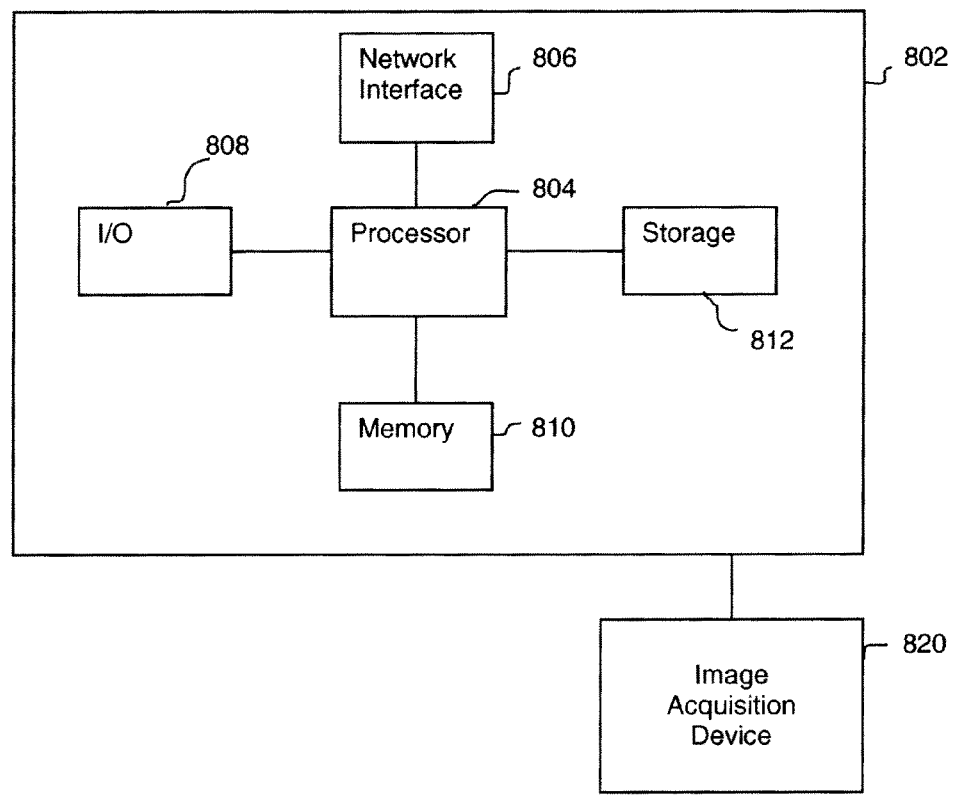
FIG. 8 is a high level block diagram of a computer capable of implementing the present invention.

A high level block diagram of such a computer is illustrated in FIG. 8. Computer 802 contains a processor 804 which controls the overall operation of the computer 802 by executing computer program instructions which define such operation. The computer program instructions may be stored in a storage device 812, or other computer readable medium, (e.g., magnetic disk) and loaded into memory 810 when execution of the computer program instructions is desired. Thus, all method steps described above, including the method steps illustrated in FIGS. 1, 3, and 5 may be defined by the computer program instructions stored in the memory 810 and/or storage 812 and controlled by the processor 804 executing the computer program instructions. An image acquisition device 820, such as an X-ray imaging device, can be connected to the computer 802 to input fluoroscopic image sequences to the computer 802. It is possible to implement the image acquisition device 820 and the computer 802 as one device. It is also possible that the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.) One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for tracking a virtual electrode (VE) on a coronary sinus (CS) catheter in a fluoroscopic image sequence comprising:
receiving user inputs indicating locations of a plurality of CS catheter electrodes and a location of a VE in a first frame of the fluoroscopic image sequence;
detecting a VE part of the CS catheter in the first frame, wherein the VE part is a segment of the CS catheter between a most proximal electrode and the VE;
initializing a catheter electrode template and a VE part template in a first frame of a fluoroscopic image sequence based on the input locations of the plurality of CS catheter electrodes and the input location of the VE in the first frame; and tracking the VE in a second frame of the fluoroscopic image sequence by:

detecting electrode position candidates and catheter body point candidates in the second frame of the fluoroscopic image sequence using respective trained detectors;

tracking the catheter electrode template in the second frame based on the detected electrode position candidates;

generating VE part hypotheses based on the most proximal electrode in the catheter electrode template in the second frame;

calculating a probability score for each of the VE part hypotheses;

selecting one of the VE part hypotheses as the VE part result in the second frame based on the probability scores; and displaying the VE part result in the second frame.

2. The method of claim 1, wherein the tracking of the VE in a second frame of the fluoroscopic image sequence further comprises:

refining the VE part result in the current frame using non-rigid tracking, wherein the refined VE part result provides a location of the VE in the second frame.

3. The method of claim 1, wherein the step of tracking the catheter electrode template in the second frame based on the detected electrode position candidates comprises:

generating catheter electrode model candidates in the second frame based on the detected electrode position candidates;

calculating a probability score for each of the catheter electrode model candidates; and selecting one of the catheter electrode model candidates based on the probability score, wherein the selected catheter electrode model candidate provides locations of the plurality of CS catheter electrodes in the second frame.

4. The method of claim 1, wherein the step of detecting a VE part of the CS catheter in the first frame comprises:

detecting a set of spline control points between the most proximal electrode and the VE, wherein a first one of the spline control points is located at the most proximal electrode and a last one of the spline control points is located at the VE.

5. The method of claim 1, wherein the step of initializing a catheter electrode template and a VE part template in a first frame of a fluoroscopic image sequence based on the input locations of the plurality of CS catheter electrodes and the input location of the VE in the first frame comprises:

determining if a length of the VE part is greater than a threshold value; and if the length of the VE part is greater than a threshold value, generating a first VE part template and a second VE part template, each having a plurality of control points, wherein:

a first control point of the first VE part template is located at the most proximal electrode and a last control point of the first VE part template is located at a maximum curvature point on the detected VE part, and a first control point of the second VE part template is located at the maximum curvature point on the detected VE part, and a last control point of the second VE part template is located at the VE.

6. The method of claim 1, wherein the step of detecting electrode position candidates and catheter body point candidates in the second frame of the fluoroscopic image sequence using respective trained detectors comprises:

detecting catheter tip candidates in the second frame using a trained catheter tip detector;

detecting electrode candidates in the second frame using a trained electrode detector; and calculating a catheter body point probability map in the second frame using a trained catheter body point detector.

7. The method of claim 1, wherein the step of generating VE part hypotheses based on the most proximal electrode in the catheter electrode template in the second frame comprises:

generating a seed hypothesis in the second frame by translating a VE part template in a previous frame of the fluoroscopic image sequence to the second frame of the fluoroscopic image sequence, such that a first control point of the translated VE part template is located at the most proximal electrode in the second frame; and generating a plurality of hypotheses from the seed hypothesis by varying affine parameters of the seed hypothesis using the location of the most proximal electrode as a transformation center.

8. The method of claim 7, wherein the previous frame is the first frame and the VE part template in the previous frame is the VE part template initialized in the first frame.

9. The method of claim 7, wherein the previous frame is a frame between the first frame and the second frame, and the VE part template in the previous frame is a VE part template previously tracked in the previous frame.

10. The method of claim 1, wherein the step of calculating a probability score for each of the VE part hypotheses comprises:

calculating a probability score based on a likelihood term and a prediction term, wherein:

the likelihood term is calculated based on a first probability score and a second probability score, the first probability score is calculated based on catheter body point detection scores of control points of the respective VE part hypothesis determined by a trained catheter body point detector, and the second probability score is calculated based on a normalized cross-correlation between intensity values of the control points of the respective VE part hypothesis in the second frame and intensity values of control points of the VE part template initialized in the first frame; and the prediction term is calculated based on a VE part template in a previous frame.

11. The method of claim 1, wherein selecting one of the VE part hypotheses as the VE part result in the second frame based on the probability score comprises:

selecting a VE part hypothesis having a highest probability score as the VE part result.

12. The non-transitory computer readable medium of claim 1, wherein selecting one of the VE part hypotheses as the VE part result in the second frame based on the probability score comprises:

selecting a VE part hypothesis having a highest probability score as the VE part result.

13. An apparatus for tracking a virtual electrode (VE) on a coronary sinus (CS) catheter in a fluoroscopic image sequence comprising:

means for detecting a VE part of the CS catheter in the first frame based on input locations of a plurality of CS catheter electrodes and an input location of VE in the first frame, wherein the VE part is a segment of the CS catheter between a most proximal electrode and the VE;
means for initializing a catheter electrode template and a VE part template in a first frame of a fluoroscopic image sequence based on the input locations of the plurality of CS catheter electrodes and the input location of the VE in the first frame; and
means for tracking the VE in a second frame of the fluoroscopic image sequence comprising:
  means for detecting electrode position candidates and catheter body point candidates in the second frame of the fluoroscopic image sequence using respective trained detectors;
  means for tracking the catheter electrode template in the second frame based on the detected electrode position candidates;
  means for generating VE part hypotheses based on the most proximal electrode in the catheter electrode template in the second frame;
  means for calculating a probability score for each of the VE part hypotheses;
  means for selecting one of the VE part hypotheses as the VE part result in the second frame based on the probability scores; and
  means for displaying the VE part result in the second frame.

14. The apparatus of claim 13, wherein the means for tracking the VE in a second frame of the fluoroscopic image sequence further comprises:
means for refining the VE part result in the current frame using non-rigid tracking, wherein the refined VE part result provides a location of the VE in the second frame.

15. The apparatus of claim 13, wherein the means for tracking the catheter electrode template in the second frame based on the detected electrode position candidates comprises:
means for generating catheter electrode model candidates in the second frame based on the detected electrode position candidates;
means for calculating a probability score for each of the catheter electrode model candidates; and
means for selecting one of the catheter electrode model candidates based on the probability score, wherein the selected catheter electrode model candidate provides locations of the plurality of CS catheter electrodes in the second frame.

16. The apparatus of claim 13, wherein the means for detecting a VE part of the CS catheter in the first frame comprises:
means for detecting a a set of spline control points between the most proximal electrode and the VE, wherein a first one of the spline control points is located at the most proximal electrode and a last one of the spline control points is located at the VE.

17. The apparatus of claim 13, wherein the means for initializing a catheter electrode template and a VE part template in a first frame of a fluoroscopic image sequence based on the input locations of the plurality of CS catheter electrodes and the input location of the VE in the first frame comprises:
means for determining if a length of the VE part is greater than a threshold value; and
means for generating a first VE part template and a second VE part template, each having a plurality of control points, when the length of the VE part is greater than the threshold, wherein:
  a first control point of the first VE part template is located at the most proximal electrode and a last control point of the first VE part template is located at a maximum curvature point on the detected VE part, and
  a first control point of the second VE part template is located at the maximum curvature point on the detected VE part, and a last control point of the second VE part template is located at the VE.

18. The apparatus of claim 13, wherein the means for detecting electrode position candidates and catheter body point candidates in the second frame of the fluoroscopic image sequence using respective trained detectors comprises:
means for detecting catheter tip candidates in the second frame using a trained catheter tip detector;
means for detecting electrode candidates in the second frame using a trained electrode detector; and
means for calculating a catheter body point probability map in the second frame using a trained catheter body point detector.

19. The apparatus of claim 13, wherein the means for generating VE part hypotheses based on the most proximal electrode in the catheter electrode template in the second frame comprises:
means for generating a seed hypothesis in the second frame by translating a VE part template in a previous frame of the fluoroscopic image sequence to the second frame of the fluoroscopic image sequence, such that a first control point of the translated VE part template is located at the most proximal electrode in the second frame; and
means for generating a plurality of hypotheses from the seed hypothesis by varying affine parameters of the seed hypothesis using the location of the most proximal electrode as a transformation center.

20. The apparatus of claim 13, wherein the means for calculating a probability score for each of the VE part hypotheses comprises:
means for calculating a probability score based on a likelihood term and a prediction term, wherein:
  the likelihood term is calculated based on a first probability score and a second probability score, the first probability score is calculated based on catheter body point detection scores of control points of the respective VE part hypothesis determined by a trained catheter body point detector, and the second probability score is calculated based on a normalized cross-correlation between intensity values of the control points of the respective VE part hypothesis in the second frame and intensity values of control points of the VE part template initialized in the first frame; and
  the prediction term is calculated based on a VE part template in a previous frame.

21. A non-transitory computer readable medium encoded with computer executable instructions for tracking a virtual electrode (VE) on a coronary sinus (CS) catheter in a fluoroscopic image sequence, the computer executable instructions defining a method comprising:
receiving user inputs indicating locations of a plurality of CS catheter electrodes and a location of a VE in a first frame of the fluoroscopic image sequence;
detecting a VE part of the CS catheter in the first frame, wherein the VE part is a segment of the CS catheter between a most proximal electrode and the VE;
initializing a catheter electrode template and a VE part template in a first frame of a fluoroscopic image sequence based on the input locations of the plurality of CS catheter electrodes and the input location of the VE in the first frame; and tracking the VE in a second frame of the fluoroscopic image sequence by:
  detecting electrode position candidates and catheter body point candidates in the second frame of the fluoroscopic image sequence using respective trained detectors;
  tracking the catheter electrode template in the second frame based on the detected electrode position candidates;
  generating VE part hypotheses based on the most proximal electrode in the catheter electrode template in the second frame;
  calculating a probability score for each of the VE part hypotheses; and
  selecting one of the VE part hypotheses as the VE part result in the second frame based on the probability scores; and
  displaying the VE part result in the second frame.

22. The non-transitory computer readable medium of claim 21, wherein the tracking of the VE in a second frame of the fluoroscopic image sequence further comprises:
  refining the VE part result in the current frame using non-rigid tracking, wherein the refined VE part result provides a location of the VE in the second frame.

23. The non-transitory computer readable medium of claim 21, wherein the step of tracking the catheter electrode template in the second frame based on the detected electrode position candidates comprises:
  generating catheter electrode model candidates in the second frame based on the detected electrode position candidates;
  calculating a probability score for each of the catheter electrode model candidates; and
  selecting one of the catheter electrode model candidates based on the probability score, wherein the selected catheter electrode model candidate provides locations of the plurality of CS catheter electrodes in the second frame.

24. The non-transitory computer readable medium of claim 21, wherein the step of detecting a VE part of the CS catheter in the first frame comprises:
  detecting a set of spline control points between the most proximal electrode and the VE, wherein a first one of the spline control points is located at the most proximal electrode and a last one of the spline control points is located at the VE.

25. The non-transitory computer readable medium of claim 21, wherein the step of initializing a catheter electrode template and a VE part template in a first frame of a fluoroscopic image sequence based on the input locations of the plurality of CS catheter electrodes and the input location of the VE in the first frame comprises:
  determining if a length of the VE part is greater than a threshold value; and
  if the length of the VE part is greater than a threshold value, generating a first VE part template and a second VE part template, each having a plurality of control points, wherein:
    a first control point of the first VE part template is located at the most proximal electrode and a last control point of the first VE part template is located at a maximum curvature point on the detected VE part, and
    a first control point of the second VE part template is located at the maximum curvature point on the detected VE part, and a last control point of the second VE part template is located at the VE.

26. The non-transitory computer readable medium of claim 21, wherein the step of detecting electrode position candidates and catheter body point candidates in the second frame of the fluoroscopic image sequence using respective trained detectors comprises:
  detecting catheter tip candidates in the second frame using a trained catheter tip detector;
  detecting electrode candidates in the second frame using a trained electrode detector; and
  calculating a catheter body point probability map in the second frame using a trained catheter body point detector.

27. The non-transitory computer readable medium of claim 21, wherein the step of generating VE part hypotheses based on the most proximal electrode in the catheter electrode template in the second frame comprises:
  generating a seed hypothesis in the second frame by translating a VE part template in a previous frame of the fluoroscopic image sequence to the second frame of the fluoroscopic image sequence, such that a first control point of the translated VE part template is located at the most proximal electrode in the second frame; and
  generating a plurality of hypotheses from the seed hypothesis by varying affine parameters of the seed hypothesis using the location of the most proximal electrode as a transformation center.

28. The non-transitory computer readable medium of claim 21, wherein the step of calculating a probability score for each of the VE part hypotheses comprises:
  calculating a probability score based on a likelihood term and a prediction term, wherein:
  the likelihood term is calculated based on a first probability score and a second probability score, the first probability score is calculated based on catheter body point detection scores of control points of the respective VE part hypothesis determined by a trained catheter body point detector, and the second probability score is calculated based on a normalized cross-correlation between intensity values of the control points of the respective VE part hypothesis in the second frame and intensity values of control points of the VE part template initialized in the first frame; and
  the prediction term is calculated based on a VE part template in a previous frame.

* * * * *